United States Patent
Zhang

(10) Patent No.: US 7,313,438 B2
(45) Date of Patent: Dec. 25, 2007

(54) SELECTIVE CHAMBER ATP PACING

(75) Inventor: Yunlong Zhang, Mounds View, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 533 days.

(21) Appl. No.: 10/858,564

(22) Filed: Jun. 1, 2004

(65) Prior Publication Data

US 2005/0267540 A1  Dec. 1, 2005

(51) Int. Cl.
*A61N 1/00* (2006.01)
(52) U.S. Cl. ....................................................... 607/14
(58) Field of Classification Search ................. 607/14, 607/18, 25, 27
See application file for complete search history.

(56) References Cited

U.S. PATENT DOCUMENTS

| | | | |
|---|---|---|---|
| 6,370,427 B1 | 4/2002 | Alt et al. | |
| 6,606,516 B2 | 8/2003 | Levine | |
| 6,748,261 B1 | 6/2004 | Kroll et al. | |
| 6,901,291 B2 * | 5/2005 | Stoop et al. | 607/27 |
| 2004/0049235 A1 | 3/2004 | Deno et al. | |
| 2005/0027323 A1 * | 2/2005 | Mulligan et al. | 607/18 |
| 2005/0209650 A1 * | 9/2005 | Van Gelder et al. | 607/25 |
| 2006/0247690 A1 | 11/2006 | Hess et al. | |

* cited by examiner

*Primary Examiner*—George Manuel
(74) *Attorney, Agent, or Firm*—Schwegman, Lundberg & Woessner, P.A.

(57) ABSTRACT

A method and system for delivering anti-tachycardia pacing (ATP) is disclosed. By comparing the time intervals between senses from both ventricles, the origin of a ventricular tachyarrhythmia may be mapped to one or the other of the ventricles. The arrhythmic ventricle may then be paced with either single-ventricle or biventricular ATP pacing.

20 Claims, 2 Drawing Sheets

SELECTIVE CHAMBER ATP PACING

FIELD OF THE INVENTION

This invention pertains to methods and system for treating cardiac arrhythmias with anti-tachycardia pacing.

BACKGROUND

Tachyarrhythmias are abnormal heart rhythms characterized by a rapid heart rate, typically expressed in units of beats per minute (bpm). Examples of tachyarrhythmias include supraventricular tachycardias (SVT's) such as sinus tachycardia, atrial tachycardia (AT), and atrial fibrillation (AF). The most dangerous tachyarrythmias, however, are ventricular tachycardia (VT) and ventricular fibrillation (VF). Ventricular rhythms occur when re-entry of a depolarizing wavefront in areas of the ventricular myocardium with different conduction characteristics becomes self-sustaining or when an excitatory focus in the ventricle usurps control of the heart rate from the sinoatrial node. The result is rapid and ineffective contraction of the ventricles out of electromechanical synchrony with the atria. Most ventricular rhythms exhibit an abnormal QRS complex in an electrocardiogram because they do not use the normal ventricular conduction system, the depolarization spreading instead from the excitatory focus or point of re-entry directly into the myocardium. Ventricular tachycardia is typically characterized by distorted QRS complexes that occur at a rapid rate, while ventricular fibrillation is diagnosed when the ventricle depolarizes in a chaotic fashion with QRS complexes of constantly changing shape. Both ventricular tachycardia and ventricular fibrillation are hemodynamically compromising, and both can be life-threatening. Ventricular fibrillation, however, causes circulatory arrest within seconds and is the most common cause of sudden cardiac death.

Cardioversion (an electrical shock delivered to the heart synchronously with the QRS complex) and defibrillation (an electrical shock delivered without synchronization to the QRS complex to terminate ventricular fibrillation) can be used to terminate most tachyarrhythmias, including SVT's, VT, and VF. The electric shock terminates the tachyarrhythmia by depolarizing all of the myocardium simultaneously and rendering it refractory. A class of cardiac rhythm management devices known as an implantable cardioverter/defibrillator (ICD) provides this kind of therapy by delivering a shock pulse to the heart when the device detects fibrillation.

Another type of electrical therapy for tachycardia is anti-tachycardia pacing (ATP). In ATP, the heart is competitively paced with one or more pacing pulses in an effort to interrupt the reentrant circuit causing the tachycardia. ATP can be applied to either the ventricles or the atria. Modern ICD's typically have ATP capability so that ATP therapy is delivered to the heart when a tachycardia is detected, while a shock pulse is delivered when fibrillation occurs. Although cardioversion/defibrillation will terminate tachycardia, it consumes a large amount of stored power from the battery and results in patient discomfort owing to the high voltage of the shock pulses. It is desirable, therefore, for the ICD to use ATP to terminate a tachyarrhythmia whenever possible. It is commonly believed that only cardioversion/defibrillation will terminate fibrillation and certain high rate tachycardias, while ATP can be used to treat lower rate tachycardias. A tachyarrhythmia that is regarded as terminable by ATP therapy, based upon rate or other factors, will be referred to herein as either a terminable tachyarrhythmia or a tachycardia.

In most ICD's with ATP capability, fibrillation (VF or AF) is distinguished from tachycardia (VT or AT) using rate-based criteria so that ATP or shock therapy can be delivered as appropriate. The ventricular heart rate is usually measured by detection of the time between successive R waves (i.e., ventricular depolarizations), and the atrial rate is measured by detection of the time between successive P waves (atrial depolarizations). A measured heart rate is classified as a tachycardia when the rate is in a tachycardia zone, defined as a range of rates above a tachycardia detection rate (TDR) but below a fibrillation detection rate (FDR). A measured heart rate above the FDR, on the other hand, is in the fibrillation zone and is classified as either atrial or ventricular fibrillation. In a typical device, a tachyarrhythmia with a heart rate in the tachycardia zone is treated with ATP therapy in order to avoid an unnecessary painful shock to the patient, and a defibrillation shock is delivered if the pacing fails to terminate the tachyarrhythmia. The present disclosure relates to a method and apparatus for delivering ATP therapy in a manner that increases the likelihood that ATP therapy will terminate a tachyarrhythmia without resorting to a defibrillation shock.

DETAILED DESCRIPTION

The mechanism by which ATP therapy converts a tachyarrhythmia is through the entrainment of the heart by a burst of pacing pulses which results in the termination of the tachyarrhythmia. For entrainment to occur, the ATP burst must penetrate into the re-entrant cycle responsible for the tachyarrhythmia. The present disclosure relates to a way of delivering ATP therapy which increases the probability that such penetration will occur by mapping the origin of the tachyarrhythmia to a particular atrium or ventricle and then delivering ATP therapy to that chamber. A description of an exemplary implementation of the technique is set forth below.

1. Hardware Platform

Figure 1:
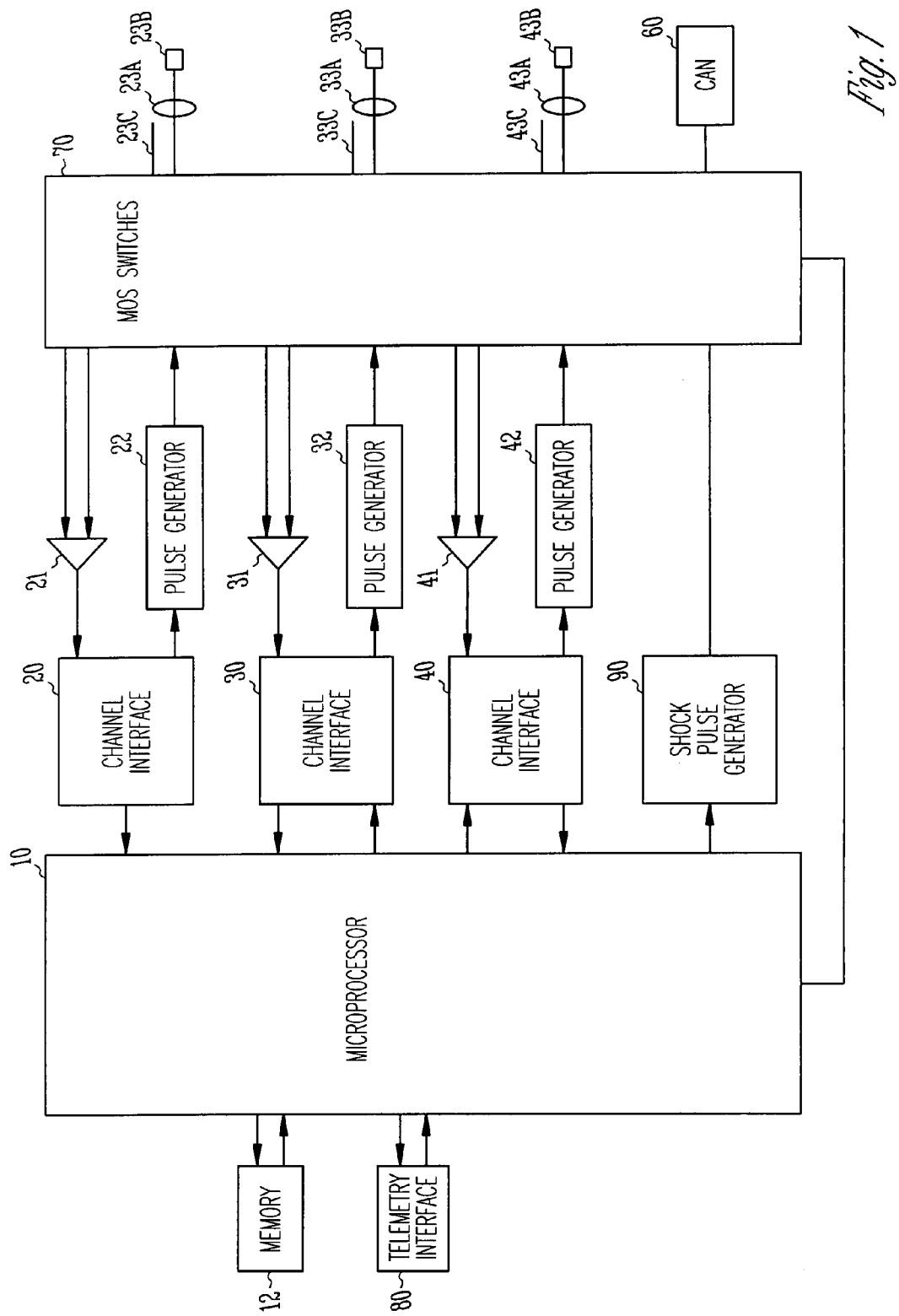
FIG. 1 is a block diagram of a cardiac rhythm management device with ATP and cardioversion/defibrillation capability and configurable for biventricular pacing.

FIG. 1 is a system diagram of a microprocessor-based cardiac rhythm management device with the capability of delivering cardioversion/defibrillation shocks as well as delivering anti-tachycardia pacing therapy to either the ventricles or the atria. The device may also be configured to deliver conventional (e.g., bradycardia) pacing as well. Such devices are usually implanted subcutaneously on the patient's chest and connected to electrodes by leads threaded through the vessels of the upper venous system into the heart. An electrode can be incorporated into a sensing channel that generates an electrogram signal representing cardiac electrical activity at the electrode site and/or incorporated into a pacing or shocking channel for delivering pacing or shock pulses to the site.

A block diagram of an implantable cardiac rhythm management device is shown in FIG. 1. The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the device so as to deliver a number of different therapies in response to detected cardiac activity. A telemetry interface 80 is also provided for enabling the controller to communicate with an external programmer or other device via a wireless telemetry link.

The device shown in FIG. 1 has three sensing/pacing channels, where a pacing channel is made up of a pulse generator connected to an electrode while a sensing channel is made up of the sense amplifier connected to an electrode. A MOS switch matrix 70 controlled by the microprocessor is used to switch the electrodes from the input of a sense amplifier to the output of a pulse generator. The switch matrix 70 also allows the sensing and pacing channels to be configured by the controller with different combinations of the available electrodes. A shock pulse generator 90 is also interfaced to the controller for delivering defibrillation shocks between an electrode and the housing or can 60 as selected by the switch matrix. In an example configuration, a sensing/pacing channel may include ring electrode 43*a* (33*a* or 23*a*) and tip electrode 43*b* (33*b* or 23*b*) of bipolar lead 43*c* (33*c* or 23*c*), sense amplifier 41 (31 or 21), pulse generator 42 (32 or 22), and a channel interface 40 (30 or 20). The channel interfaces communicate bi-directionally with a port of microprocessor 10 and may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In the illustrated embodiment, the device is equipped with bipolar leads that include two electrodes which are used for outputting a pacing pulse and/or sensing intrinsic activity. Other embodiments may employ unipolar leads with single electrodes for sensing and pacing which are referenced to the device housing or can 60 (or another electrode) by the switch matrix 70. The channels may be configured as either atrial or ventricular channels so as to enable either biatrral or biventricular pacing. For example, a configuration for biventricular sensing/pacing could have one lead of a channel disposed in the right ventricle for right ventricular sensing/pacing and another lead of a channel disposed in the coronary sinus for left ventricular sensing/pacing.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The sensing circuitry of the pacemaker detects a chamber sense when an electrogram signal (i.e., a voltage sensed by an electrode representing cardiac electrical activity) generated by a particular channel exceeds a specified intrinsic detection threshold. A chamber sense may be either an atrial sense or a ventricular sense depending on whether it occurs in the atrial or ventricular sensing channel. By measuring the intervals between chamber senses, the device is able to determine an atrial or ventricular rate, and pacing algorithms used in particular pacing modes employ such senses to trigger or inhibit pacing. Both bradycardia and anti-tachycardia pacing modes may be implemented in code executed by the controller.

2. Anti-tachycardia Pacing

The cardiac rhythm management device of FIG. 1 may be programmed with a plurality of selectable ATP pacing protocols that define the manner in which anti-tachycardia pacing is delivered. In a microprocessor-based device, the output of pacing pulses is controlled by a pacing routine that implements the selected pacing protocol as defined by various parameters. A data structure stored in memory contains the parameter sets that define each of the available pacing protocols. Pacing protocols for ATP therapy attempt to block the reentrant depolarization wavefront causing the tachycardia with depolarizing wavefronts produced by a burst of pacing pulses. (A burst, as the term is used herein, may consist of one or more pacing pulses.) Protocols may vary according to parameters that define the number of pulses delivered and the particular timing employed. For example, the protocol may define a burst of pulses delivered at a specified pacing interval (or with varying pacing intervals) and for a specified time. The protocol may further define the duration and amplitude of the pacing pulses. Different protocols are apt to be more successful than others in terminating particular tachyarrhythmias that may differ as to rate and/or depolarization pattern. For this reason, modern cardiac rhythm management devices are capable of employing a number of different ATP protocols to deliver therapy.

The device delivers ATP therapy or a defibrillation shock under programmed control of the microprocessor in response to sensed activity from the sensing channels. A sensing routine analyzes the electrical activity received from the sensing channels in order to detect a tachyarrhythmia, and the tachyarrhythmia is then classified as a tachycardia (i.e., a terminable tachyarrhythmia) or fibrillation based upon rate and/or other criteria. The device detects a ventricular tachyarrhythmia, for example, by counting ventricular senses received via the ventricular sensing channel in order to measure the heart rate and determine whether the rate exceeds a selected threshold value. Once a tachyarrhythmia is detected, the rhythm is classified into either a tachycardia or a fibrillation zone by comparing the heart rate to a fibrillation rate boundary or by other means such as assessing the stability of the rhythm. If the tachyarrhythmia is classified as terminable, a pacing routine executed by the microprocessor delivers ATP pulses in accordance with the parameters of a selected protocol.

As noted above, the object of anti-tachycardia pacing is to create one or more pace-induced wavefronts that propagate into the re-entrant circuit of the tachycardia and extinguish it. In order for a pacing pulse to terminate a tachyarrhythmia, the pulse must capture the ventricle so that a propagating depolarization results which then penetrates into the re-entrant cycle. This is complicated by the fact that during a ventricular tachyarrhythmia, the action potential consumes a large portion of the total cycle length, leaving only a small window of time when the ventricle is non-refractory and even less time for an induced depolarization wavefront to propagate into the re-entrant circuit. One adjustable ATP parameter is the coupling interval, which is the time from the last sensed depolarization to the first pacing pulse of a burst, commonly selected to be between 120 and 750 milliseconds. For capture to be achieved by that pacing pulse, the end of the coupling interval must occur when the ventricle is non-refractory. In a so-called scan mode, some devices vary the coupling interval of a series of bursts in a predetermined manner. When the ATP pacing burst consists of a train of pulses, the time between the pulses or cycle length is another parameter that can be adjusted as in a ramp-type burst where the cycle length increases or decreases with each pulse of the train.

3. Selection of ATP Pacing Site

Even if the end of the coupling interval occurs during a non-refractory period, the wavefront induced by the pacing pulse must still penetrate into the region of the heart where the re-entrant cycle is occurring in order to extinguish it. The probability of successful penetration can be increased by delivering the ATP pulses to a site near the origin of the tachyarrhythmia. A device with biventricular pacing/sensing capability may locate an arrhythmia site to one or the other ventricles and then deliver ATP pulses to that ventricle. The device maps the arrhythmic origin by measuring the interval between successive right and left ventricular senses (RV-LV interval) and the interval between successive left and right ventricular senses (LV-RV interval) during the ventricular tachyarrhythmia. A plurality of such intervals may be averaged to give representative RV-LV and LV-RV intervals. If the RV-LV interval is less than the LV-RV interval, the origin of the tachyarrhythmia is deemed to be the right ventricle, while if the RV-LV interval is greater than the LV-RV interval, the origin of the tachyarrhythmia is deemed to be the left ventricle. ATP pulses can then be delivered as left ventricular pacing pulses if the origin of the tachyarrhythmia is in the left ventricle or as right ventricular pacing pulses if the origin of the tachyarrhythmia is in the right ventricle. Alternatively, ATP pulses can be delivered as biventricular pacing pulses with an offset such that the left ventricle is paced first if the origin of the tachyarrhythmia is in the left ventricle or such that the right ventricle is paced first if the origin of the tachyarrhythmia is in the right ventricle. If there is insufficient difference between the RV-LV and LV-RV intervals (i.e., the difference is less than some predetermined threshold value), or if sensing in one of the ventricles is compromised, the origin of the tachyarrhythmia may be deemed to be indeterminate. In that case, the ATP pulses may be delivered in a pre-selected mode such as either right ventricular pacing or biventricular pacing. When there is insufficient difference between the RV-LV and LV-RV intervals, the biventricular pacing may be delivered with no offset such that both ventricles are paced simultaneously. The coupling interval may be measured with respect to a sense in one or the other ventricles always (e.g., the right ventricle) or may be measured with respect to a sense in the ventricle designated as the arrhythmic origin (i.e., the coupling interval is measured with respect to a sense in the ventricle which is to be paced or which is to be paced first in the case of biventricular pacing). Also, the particular ATP protocol employed may be selected in accordance with whether the ATP burst are delivered as right ventricular, left ventricular, or biventricular pacing pulses. Finally, although the discussion above has only dealt specifically with ventricular tachyarrhythmias and ventricular ATP therapy, it should be appreciated that atrial tachyarrhythmias may be treated in a similar manner by delivering atrial ATP therapy as left atrial, right atrial, bi-atrial pacing.

Figure 2:
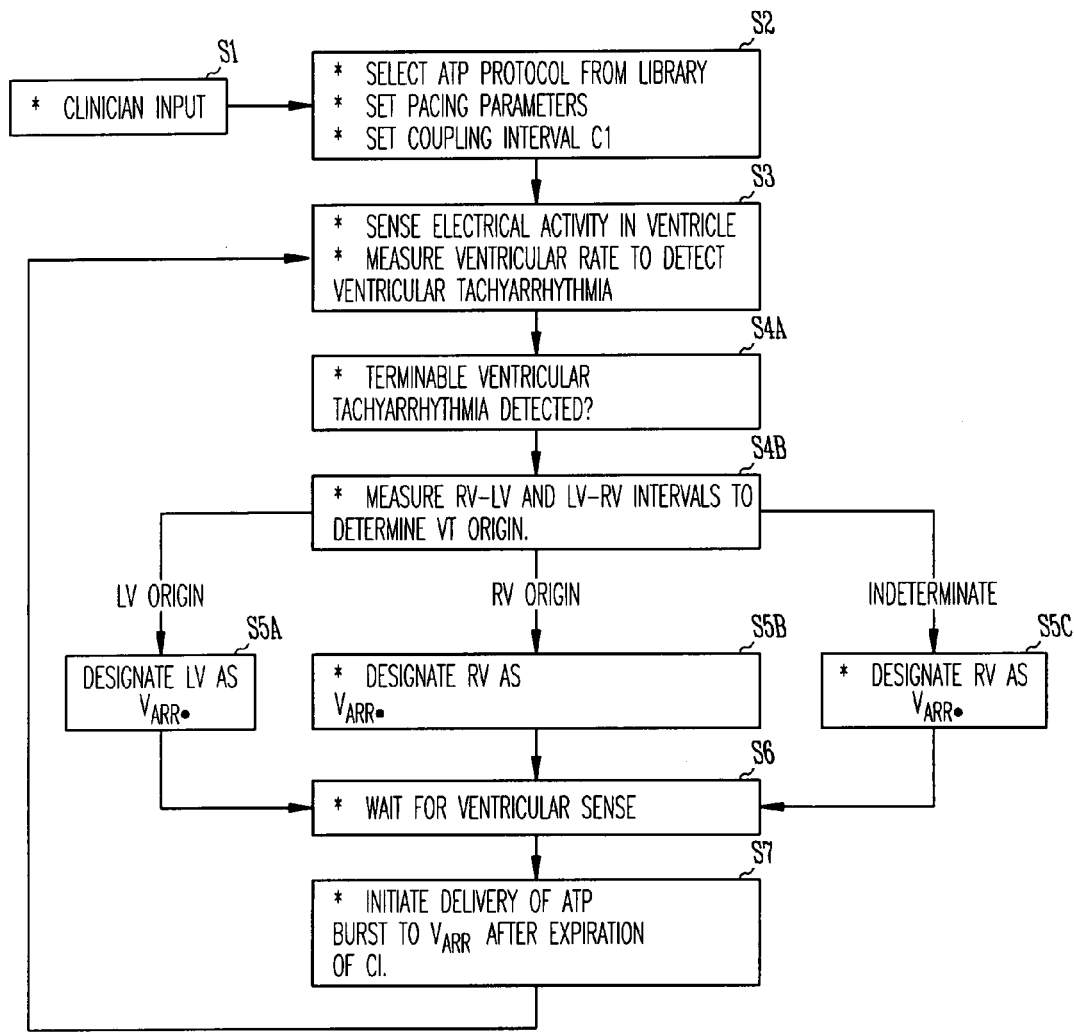
FIG. 2 is a flow diagram showing the steps performed in a particular implementation.

FIG. 2 is a flow diagram showing the steps performed by a cardiac rhythm management device in accordance with one particular algorithm for delivering ventricular ATP therapy. The device is set up for delivering anti-tachycardia pacing therapy at step S2 where particular ATP protocols are selected and various pacing parameter values are set, including the coupling interval CI. Clinician input for the set up procedure may be received via telemetry at step S1. At step S3, the device begins monitoring electrical activity in the ventricles via sensing channels and counts ventricular senses to determine the ventricular rate. Using a rate-based criterion, the ventricular rate is classified as a terminable tachyarrhythmia when it falls within a specified zone. If a terminable tachyarrhythmia is detected at step S4a, the device prepares to deliver ATP therapy. From measured RV-LV and LV-RV intervals, the device determines at step S4b which ventricle is the origin of the tachyarrhythmia. At steps S5a and S5b, the device then designates either the right or left ventricle as the arrhythmic ventricle $V_{ARR}$ according to the interval criterion. If the RV-LV and LV-RV intervals are insufficiently different, the right ventricle is designated as the arrhythmic ventricle $V_{ARR}$ in this particular embodiment. The device then waits for the next ventricular sense at step S6 and starts a timer for the coupling interval CI. After expiration of the coupling interval, an ATP burst is delivered at step S7. The device then returns to monitoring at step S3 to determine whether the tachyarrhythmia has been terminated or repetition of the therapy is necessary.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A method for delivery of anti-tachycardia pacing (ATP) therapy by a cardiac rhythm management device, comprising:
    generating electrogram signals from both the right and left ventricles and detecting a sense when the electrogram signal exceeds a specified threshold;
    detecting a ventricular tachyarrhythmia when a rate at which ventricular senses are detected exceeds a tachyarrhythmia threshold value;
    measuring an RV-LV interval as the interval between successive right and left ventricular senses and an LV-RV interval as the interval between successive left and right ventricular senses;
    delivering a burst of one or more ATP pulses in accordance with a selected ATP protocol, wherein the ATP pulses are delivered to the right ventricle if RV-LV interval is less than the LV-RV interval and to the left ventricle if the RV-LV interval is greater than the LV-RV interval.

2. The method of claim 1 further comprising delivering biventricular ATP pulses if there is an insufficient difference between the RV-LV and LV-RV intervals.

3. The method of claim 1 further comprising delivering right ventricular ATP pulses if there is an insufficient difference between the RV-LV and LV-RV intervals.

4. The method of claim 1 wherein the RV-LV and LV-RV intervals are averages of a plurality of intervals.

5. The method of claim 1 wherein the ATP burst is output after a specified coupling interval with respect to a ventricular sense in the ventricle to be paced.

6. The method of claim 1 wherein the ATP protocol is selected in accordance with whether the ATP pulses are delivered as left ventricular, right ventricular, or biventricular pacing.

7. A cardiac rhythm management device, comprising:
sensing channels for generating electrogram signals from both the right and left ventricles and detecting a sense when the electrogram signal exceeds a specified threshold;
circuitry for detecting a ventricular tachyarrhythmia when a rate at which ventricular senses are detected exceeds a tachyarrhythmia threshold value;
circuitry for measuring an RV-LV interval as the interval between successive right and left ventricular senses and an LV-RV interval as the interval between successive left and right ventricular senses;
circuitry for delivering a burst of one or more ATP pulses in accordance with a selected ATP protocol, wherein the ATP pulses are delivered to the right ventricle if RV-LV interval is less than the LV-RV interval and to the left ventricle if the RV-LV interval is greater than the LV-RV interval.

8. The device of claim 7 further comprising circuitry for delivering biventricular ATP pulses if there is an insufficient difference between the RV-LV and LV-RV intervals.

9. The device of claim 7 further comprising circuitry for delivering right ventricular ATP pulses if there is an insufficient difference between the RV-LV and LV-RV intervals.

10. The device of claim 7 wherein the RV-LV and LV-RV intervals are averages of a plurality of intervals.

11. The device of claim 7 wherein the ATP burst is output after a specified coupling interval with respect to a ventricular sense in the ventricle to be paced.

12. The device of claim 7 wherein the ATP protocol is selected in accordance with whether the ATP pulses are delivered as left ventricular, right ventricular, or biventricular pacing.

13. A method for delivery of anti-tachycardia pacing (ATP) therapy by a cardiac rhythm management device, comprising:
generating electrogram signals from both the right and left ventricles and detecting a sense when the electrogram signal exceeds a specified threshold;
detecting a ventricular tachyarrhythmia when a rate at which ventricular senses are detected exceeds a tachyarrhythmia threshold value;
measuring an RV-LV interval as the interval between successive right and left ventricular senses and an LV-RV interval as the interval between successive left and right ventricular senses;
delivering a burst of one or more biventricular ATP pulses in accordance with a selected ATP protocol, wherein the biventricular ATP pulses are delivered with an offset such that the right ventricle is paced first if the RV-LV interval is less than the LV-RV interval and the left ventricle is paced first if the RV-LV interval is greater than the LV-RV interval.

14. The method of claim 13 further comprising delivering biventricular ATP pulses with no offset such that both ventricles are paced simultaneously if there is an insufficient difference between the RV-LV and LV-RV intervals.

15. The method of claim 13 wherein the RV-LV and LV-RV intervals are averages of a plurality of intervals.

16. The method of claim 13 wherein the ATP burst is output after a specified coupling interval with respect to a ventricular sense in the ventricle which is to be paced first.

17. A cardiac rhythm management device, comprising:
sensing channels for generating electrogram signals from both the right and left ventricles and detecting a sense when the electrogram signal exceeds a specified threshold;
circuitry for detecting a ventricular tachyarrhythmia when a rate at which ventricular senses are detected exceeds a tachyarrhythmia threshold value;
circuitry for measuring an RV-LV interval as the interval between successive right and left ventricular senses and an LV-RV interval as the interval between successive left and right ventricular senses;
circuitry for delivering a burst of one or more biventricular ATP pulses in accordance with a selected ATP protocol, wherein the biventricular ATP pulses are delivered with an offset such that the right ventricle is paced first if the RV-LV interval is less than the LV-RV interval and the left ventricle is paced first if the RV-LV interval is greater than the LV-RV interval.

18. The device of claim 17 further comprising circuitry for delivering biventricular ATP pulses with no offset such that both ventricles are paced simultaneously if there is an insufficient difference between the RV-LV and LV-RV intervals.

19. The device of claim 17 wherein the RV-LV and LV-RV intervals are averages of a plurality of intervals.

20. The device of claim 17 further comprising circuitry for outputting the ATP burst after a specified coupling interval with respect to a ventricular sense in the ventricle which is to be paced first.

* * * * *